United States Patent [19]

Harrington et al.

[11] Patent Number: 6,136,971
[45] Date of Patent: Oct. 24, 2000

[54] PREPARATION OF SULFONAMIDES

[75] Inventors: Peter J. Harrington; Hiralal N. Khatri, both of Louisville; Bradley S. Dehoff, Longmont, all of Colo.

[73] Assignee: Roche Colorado Corporation, Boulder, Colo.

[21] Appl. No.: 09/354,943

[22] Filed: Jul. 15, 1999

Related U.S. Application Data

[60] Provisional application No. 60/093,220, Jul. 17, 1998.

[51] Int. Cl.$^7$ .................................................. C07D 413/00
[52] U.S. Cl. ...................... 544/122; 544/122; 544/123; 544/277; 544/284; 544/295; 544/298; 544/309; 544/310; 544/311; 544/321; 544/323; 544/324; 544/325; 544/327
[58] Field of Search ..................... 544/122, 123, 544/277, 284, 295, 298, 309, 310, 311, 321, 323, 324, 325, 327

[56] References Cited

U.S. PATENT DOCUMENTS

| | | | |
|---|---|---|---|
| 5,292,740 | 3/1994 | Burri et al. | 514/256 |
| 5,696,116 | 12/1997 | Clozel et al. | 514/221 |
| 5,728,706 | 3/1998 | Yamada et al. | 514/269 |
| 5,856,484 | 1/1999 | Breu et al. | 544/319 |

*Primary Examiner*—Mukund J. Shah
*Assistant Examiner*—Ben Schroeder
*Attorney, Agent, or Firm*—Townsend and Townsend and Crew LLP

[57] ABSTRACT

The present invention provides a process for preparing 1,2-diheteroethylene sulfonamide of the formula:

by reacting a pyrimidine monohalide of the formula:

with a mono-protected 1,2-diheteroethylene anion of the formula $M_1XCH_2CH_2YR_5$ and removing the protecting group, wherein $R_1$, $R_2$, $R_3$, $R_4$, $R_5$, $R_6$, $R_7$, $R_8$, $R_9$, Z, X, Y, M, $M_1$ and W are defined herein.

30 Claims, 1 Drawing Sheet

US 6,136,971

PREPARATION OF SULFONAMIDES

CROSS-REFERENCE TO RELATED APPLICATIONS

This application claims the benefit of U.S. Provisional Application No. 60/093,220, filed Jul. 17, 1998.

FIELD OF THE INVENTION

The present invention relates to a process for preparing ethylene glycol sulfonamide derivatives.

BACKGROUND OF THE INVENTION

Sulfonamides of the formula:

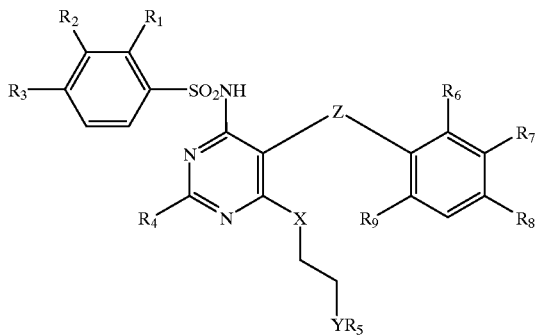

having a 1,2-diheteroethylene substituent (i.e., an ethylene group containing heteroatom substituents on 1- and 2-positions) on the pyrimidine ring moiety, such as Bosentan, have a wide variety of biological activities including inhibiting the renin angiotensin system and acting as an endothelin antagonist. These compounds are useful in treatment of a variety of illnesses including cardiovascular disorders such as hypertension, ischemia, vasospasms and angina pectoris.

A current method of preparing ethylene glycol sulfonamide derivatives involves reacting an appropriately substituted pyrimidine monohalide with a monoanion ethylene glycol (e.g., sodium ethylene glycol) typically using ethylene glycol as a solvent. However, one of the disadvantages of using a monoanion of ethylene glycol is the formation of undesired ethylene glycol bis-sulfonamide in which two molecules of the pyrimidine monohalide are coupled with one molecule of ethylene glycol. The formation of this bis-sulfonamide compound requires costly and laborious separation steps to obtain a pharmaceutically suitable pure ethylene glycol sulfonamide compound. In addition, the use of ethylene glycol as a solvent, which is acceptable in a small scale reaction, is impracticable in a large industrial scale synthesis because of its toxicity and its high boiling point which requires a large amount of time and high energy consumption to remove it by distillation.

Another drawback to the current synthesis is the need for isolating a pyrimidine dihalide (W=halide) of the formula:

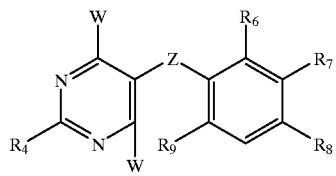

which is believed to be a potent sensitizer. This problem is further complicated by the use of a halogenated solvent, e.g., methylene chloride, during the isolation of pyrimidine dihalide. Halogenated solvent is expensive to dispose of properly, thus leading to an added cost.

Furthermore, the current synthesis requires at least six separate isolation steps and the use of many different solvents, which makes it economically less attractive as an industrial process.

Therefore, there is a need for a process for preparing the above described 1,2-diheteroethylene sulfonamides with a reduced number of reaction product isolation steps. There is a need for a process for preparing the 1,2-diheteroethylene sulfonamides which does not produce undesired 1,2-diheteroethylene bis-sulfonamides. There is a need for a process for preparing the 1,2-diheteroethylene sulfonamides which does not require isolation of potent sensitizers such as pyrimidine dihalide and/or pyrimidine monohalide intermediates.

SUMMARY OF THE INVENTION

The present invention provides a process for preparing a mono-protected 1,2-diheteroethylene substituted sulfonamide of the formula:

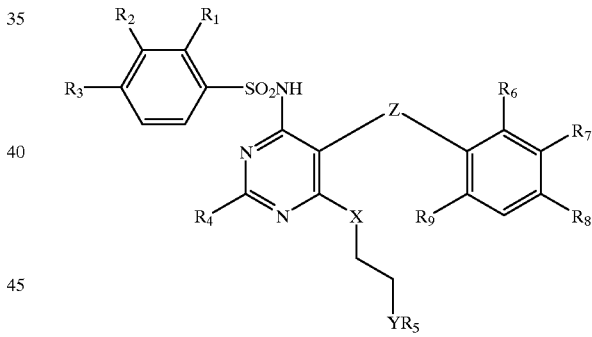

by contacting a pyrimidine monohalide of the formula:

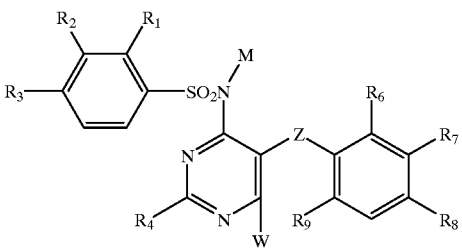

with a mono-protected 1,2-diheteroethylene anion of the formula $M_1XCH_2CH_2YR_5$, wherein $R_1$ is hydrogen, lower alkyl, lower alkoxy, lower alkylthio, halogen or trifluoromethyl;

$R_2$ is hydrogen, halogen, lower alkoxy, trifluoromethyl or $OCH_2COOR_a$;

$R_3$ is hydrogen, halogen, lower alkyl, lower alkylthio, trifluoromethyl, cycloalkyl, lower alkoxy or trifluoromethoxy; or $R_2$ and $R_3$ together can be butadienyl, methylenedioxy, ethylenedioxy or isopropylidenedioxy;

$R_4$ is hydrogen, lower alkyl, cycloalkyl, trifluoromethyl, lower alkoxy, lower alkylthio, lower alkylthio-lower alkyl, hydroxy-lower alkyl, hydroxy-lower alkoxy, lower alkoxy-lower alkyl, hydroxy-lower alkoxy-lower alkyl, hydroxy-lower alkoxy-lower alkoxy, lower alkylsulfinyl, lower alkylsulfonyl, 2-methoxy-3-hydroxypropoxy, 2-hydroxy-3-phenylpropyl, amino-lower alkyl, lower alkylamino-lower alkyl, di-lower alkylamino-lower alkyl, amino, lower alkylamino, di-lower alkylamino, arylamino, aryl, arylthio, aryloxy, aryl-lower alkyl or heterocyclyl;

$R_5$ is a protecting group;

$R_6$, $R_7$, $R_8$ and $R_9$ are independently hydrogen, halogen, lower alkyl, trifluoromethyl, lower alkoxy, lower alkylthio, hydroxy, hydroxymethyl, cyano, carboxyl, formyl, methylsulfinyl, methylsulfonyl, methylsulfonyloxy or lower alkyloxy-carbonyloxy; or $R_7$ together with $R_6$ or $R_8$ can be butadienyl, methylenedioxy, ethylenedioxy or isopropylidenedioxy;

Z is O, S, ethylene, vinylene, C(=O), OCHR$_{10}$, or SCHR$_{10}$;

$R_{10}$ is hydrogen or lower alkyl;

X and Y are independently O, S, or NH;

M is hydrogen, an alkaline metal or an alkaline earth metal;

$M_1$ is an alkaline metal or an alkaline earth metal; and

W is a halide.

Preferably, the reaction is conducted in a nonpolar aprotic solvent. The present invention also provides a method for removing the protecting group, $R_5$.

In one aspect of the invention, X and Y are O and the protecting group, $R_5$, is a tert-butyl group which is used to protect the hydroxy group of ethylene glycol as an ether. The tert-butyl group of an ether is then removed using a formic acid to produce a formyloxy-protected ethylene glycol sulfonamide derivative ($R_5$=CHO). Treatment of this compound with a base then produces an ethylene glycol sulfonamide derivative containing a free hydroxy group.

The present invention also provides a process for producing the pyrimidine monohalide by contacting a pyrimidine dihalide of the formula:

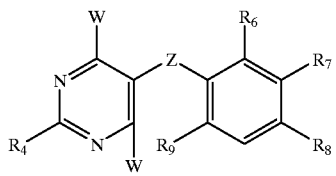

with a sulfonamide of the formula:

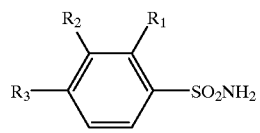

This coupling reaction is preferably conducted in a nonpolar solvent and is facilitated by the presence of a base and a phase transfer catalyst which increases the rate of reaction. It should be appreciated that when a base is present, the actual compound which is contacted with the pyrimidine dihalide may be the anion of the sulfonamide. By using the same reaction solvent in this reaction as the subsequent reaction, a need for isolation and/or purification of pyrimidine monohalide is avoided. As used herein, the term "isolation" of a compound refers to concentrating or separating the reaction product or a resulting work-up product such that the resulting composition, including any solvent that may be present, comprises at least about 80% of the compound, preferably at least about 90% of the compound, and more preferably at least about 95% of the compound. The term "purification" refers to a process for separating the desired compound from undesired compounds. A purity of a compound refers to the amount of the desired compound present in the mixture, not including any solvent which may also be present. Thus, a 90% pure compound dissolved in a large volume of solvent may still be considered to be 90% pure, but it may not be considered to be "isolated" since there is a large amount of solvent still present.

Isolation and/or purification of each product in the reaction is avoided by using a nonpolar solvent as the reaction solvent. Preferably the nonpolar solvent is an aprotic solvent, such as an ether and a hydrocarbon, more preferably the nonpolar solvent is selected from the group consisting of toluene, tetrahydrofuran and 2-methyltetrahydrofuran, and most preferably the nonpolar solvent is toluene.

Another aspect of the present invention is production of the pyrimidine dihalide by contacting a pyrimidinedione of the formula:

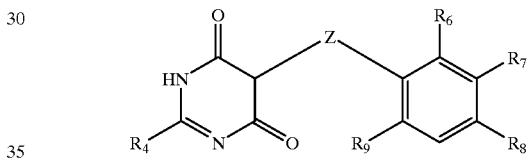

with a dehydrohalogenating agent. The product, pyrimidine dihalide, is a potent sensitizer, and the process of the present invention allows using the pyrimidine dihalide in the subsequent process without the need for isolation.

The present invention is particularly useful in the synthesis of an ethylene glycol sulfonamide derivative of the formula:

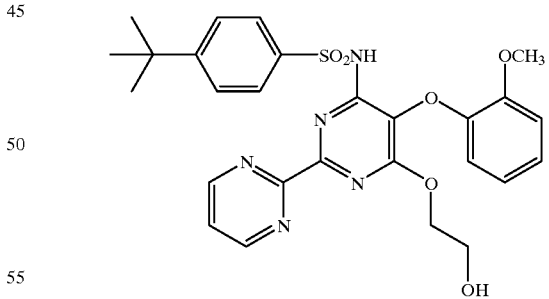

from the corresponding starting materials.

Another embodiment of the present invention provides new chemical compounds p-tert-butyl-N-[6-(2-tert-butoxyethoxy)-5-(o-methoxyphenoxy)-2-(pyrimidin-2-yl)-pyrimidin-4-yl] benzenesulfonamide, p-tert-butyl-N-[6-(2-formyloxyethoxy)-5-(o-methoxyphenoxy)-2-(pyrimidin-2-yl)-pyrimidin-4-yl] benzenesulfonamide, p-tert-butyl-N-[6-(2-formyloxyethoxy)-5-(o-methoxyphenoxy)-2-(pyrimidin-2-yl)-pyrimidin-4-yl] benzenesulfonamide monoethyl alcohol solvate in a crystalline form and p-tert-butyl-N-[6- chloro-5-(o-methoxyphenoxy)-2-(pyrimidin-2-yl)-pyrimidin-4-yl] benzenesulfonamide potassium salt.

DETAILED DESCRIPTION OF THE INVENTION

Figure 1:
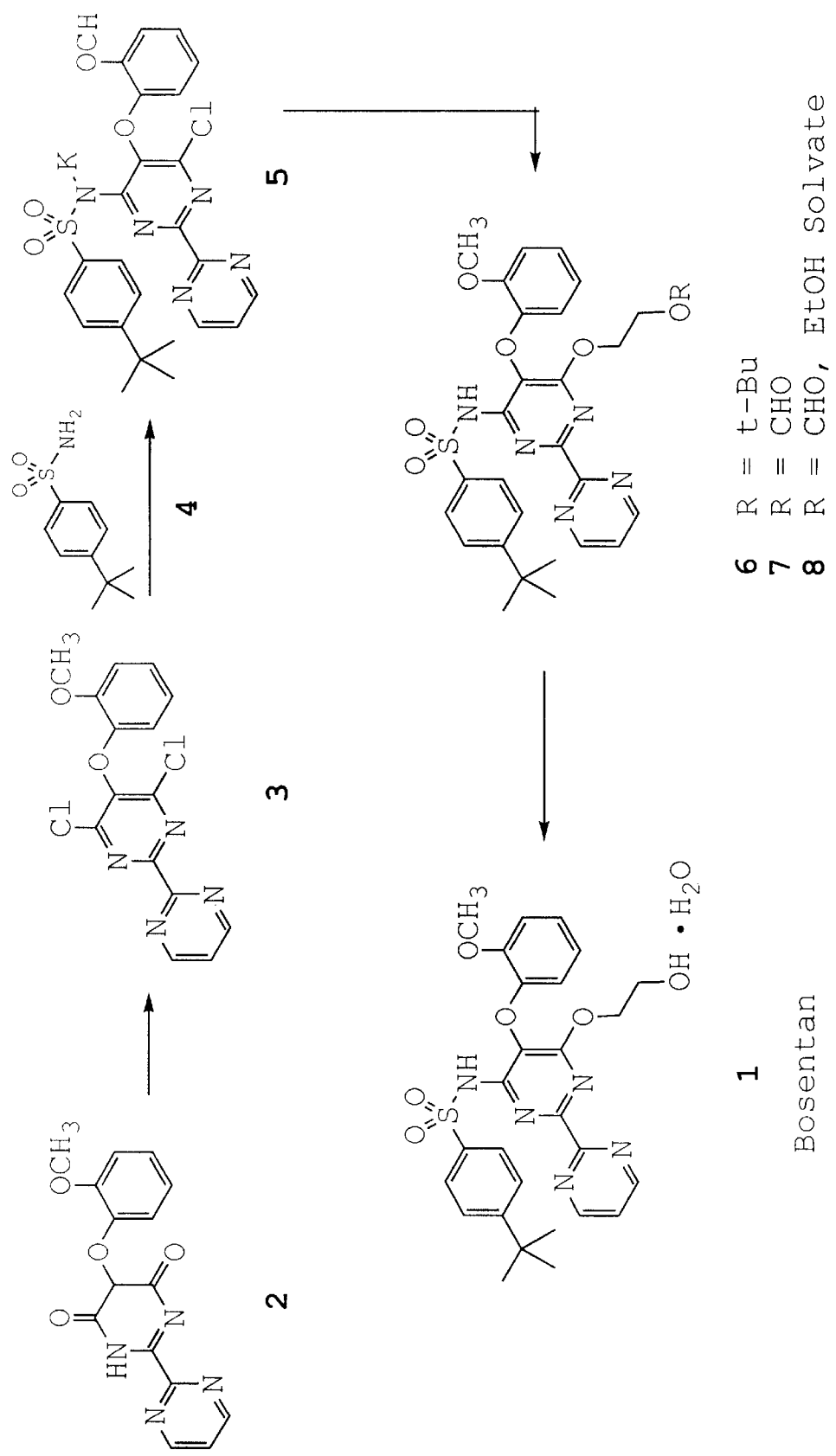
FIG. 1 shows one embodiment of a reaction scheme of the present invention for preparing Bosentan.

The present invention provides a process for preparing mono-protected 1,2-diheteroethylene sulfonamide of the formula I and their hydrates:

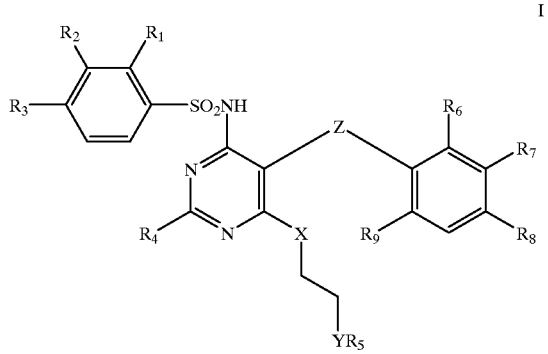

I wherein $R_1$ is hydrogen, lower alkyl, lower alkoxy, lower alkylthio, halogen or trifluoromethyl;

$R_2$ is hydrogen, halogen, lower alkoxy, trifluoromethyl or $OCH_2COOR_a$;

$R_3$ is hydrogen, halogen, lower alkyl, lower alkylthio, trifluoromethyl, cycloalkyl, lower alkoxy or trifluoromethoxy; or $R_2$ and $R_3$ together can be butadienyl, methylenedioxy, ethylenedioxy or isopropylidenedioxy;

$R_4$ is hydrogen, lower alkyl, cycloalkyl, trifluoromethyl, lower alkoxy, lower alkylthio, lower alkylthio-lower alkyl, hydroxy-lower alkyl, hydroxy-lower alkoxy, lower alkoxy-lower alkyl, hydroxy-lower alkoxy-lower alkyl, hydroxy-lower alkoxy-lower alkoxy, lower alkylsulfinyl, lower alkylsulfonyl, 2-methoxy-3-hydroxypropoxy, 2-hydroxy-3-phenylpropyl, amino-lower alkyl, lower alkylamino-lower alkyl, di-lower alkylamino-lower alkyl, amino, lower alkylamino, di-lower alkylamino, arylamino, aryl, arylthio, aryloxy, aryl-lower alkyl or heterocyclyl;

$R_5$ is a protecting group;

$R_6$, $R_7$, $R_8$ and $R_9$ are independently hydrogen, halogen, lower alkyl, trifluoromethyl, lower alkoxy, lower alkylthio, hydroxy, hydroxymethyl, cyano, carboxyl, formyl, methylsulfinyl, methylsulfonyl, methylsulfonyloxy or lower alkyloxy-carbonyloxy; or $R_7$ together with $R_6$ or $R_8$ can be butadienyl, methylenedioxy, ethylenedioxy or isopropylidenedioxy;

Z is O, S, ethylene, vinylene, C(=O), $OCHR_{10}$, or $SCHR_{10}$;

$R_{10}$ is hydrogen or lower alkyl; and

X and Y are independently O, S, or NH; and salts thereof.

The process of the present invention provides many advantages and improvements over the current processes of synthesizing the above defined 1,2-diheteroethylene sulfonamide compounds.

The term "lower", as used herein, denotes groups with 1–7 carbon atoms, preferably 1–4 carbon atoms. Alkyl, alkoxy and alkylthio groups as well as alkyl groups as components of alkanoyl groups can be straight-chain or branched. Methyl, ethyl, propyl, isopropyl, butyl, sec- and tert-butyl are examples of such alkyl groups. Halogen denotes fluorine, chlorine, bromine and iodine, with chlorine being preferred. Cycloalkyl denotes residues with 3 to 8 carbon atoms, such as cyclopropyl, cyclobutyl, cyclopentyl or cyclohexyl, and the like. Examples of aryl residues are phenyl and substituted phenyl residues, with halogen, lower alkyl, lower alkoxycarboxyl and trifluoromethyl especially coming into consideration as substituents. Examples of heterocyclyl residues are unsubstituted or, preferably, substituted (for example, mono- or disubstituted with lower alkyl, lower alkoxy, halogen, aryl, aryl-lower alkyl or mixtures thereof) mono- or bicyclic 5- and 6-membered heterocyclic residues with oxygen, nitrogen or sulfur as the hetero atom, such as, for example, 2- and 3-furyl, pyrimidinyl, 2-, 3- and 4-pyridyl and pyridyl N-oxide, 1,2- and 1,4-diazinyl, morpholino, 2- and 3-thienyl, isoxazolyl, oxazolyl, imidazolyl, pyrrolyl, benzofuranyl, benzothienyl, indolyl, purinyl, quinolyl, isoquinolyl, quinazolyl, and the like.

With respect to compound I:

Preferably, Z is O and, furthermore, $R_6$ is lower alkoxy, especially methoxy, and $R_7$, $R_8$ and $R_9$ are hydrogen.

$R_5$ is a protecting group. It will be recognized that the identity of the protecting group depends on the identity of the Y moiety. Thus, for example, when Y is NH then $R_5$ is an amine protecting group, when Y is S then $R_5$ is a thiol protecting group and when Y is O then $R_5$ is a hydroxy protecting group. Suitable protecting groups for a given Y moiety are well known to one of ordinary skill in the art, and some of the representative suitable protecting groups are disclosed in "Protecting Groups in Organic Synthesis," T.W. Greene, John Wiley & Sons, New York, N.Y., 1981, which is incorporated herein in its entirety. Preferably, when X and Y are O, $R_5$ is tert-butyl.

$R_1$ and $R_2$ are preferably hydrogen.

$R_3$ is preferably lower alkyl, more preferably t-butyl.

$R_4$ is preferably 2-pyrimidinyl.

X and Y are preferably oxygen.

The process of the present invention includes contacting a pyrimidine monohalide of the formula II:

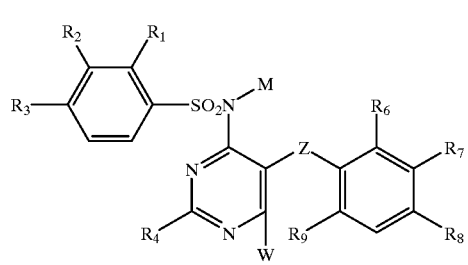

II with a mono-protected 1,2-diheteroethylene anion of the formula $M_1XCH_2CH_2YR_5$ to produce the mono-protected 1,2-diheteroethylene sulfonamide I. M is hydrogen or a metal, preferably hydrogen, an alkali metal or alkali-earth metal, and more preferably hydrogen or an alkali metal. Still more preferably M is selected from the group consisting of hydrogen, sodium, lithium and potassium, and most preferably M is selected from the group consisting of hydrogen, sodium, and potassium. $M_1$ is a metal, preferably an alkali metal or alkali-earth metal, more preferably an alkali metal. Still more preferably $M_1$ is selected from the group consisting of lithium, potassium and sodium, and most preferably $M_1$ is sodium. A preferred reaction temperature is from about 15° C. to about 100° C., more preferably from about 30° C. to about 80° C., and most preferably from about 50° C. to about 60° C. A preferred reaction time is from about 1 to about 15 hours, more preferably from about 2 to about 10 hours, and most preferably from about 3 to about 7 hours. Preferably from about 1 equivalents (eq.) to about 10 eq. of mono-protected 1,2-diheteroethylene anion relative to the pyrimidine monohalide II is used in the reaction, more preferably from about 1 eq. to about 5 eq., and most preferably from about 1 eq. to about 1.2 eq.

The mono-protected 1,2-diheteroethylene anion can be prepared prior to being added to the pyrimidine monohalide II, or it can be generated in situ by contacting the compound of the formula $HXCH_2CH_2YR_5$ with a base. It will be appreciated that any base which can deprotonate $HXCH_2CH_2YR_5$ can be used. Preferably the base is selected from the group consisting of hydroxides such as sodium hydroxide, calcium hydroxide, magnesium hydroxide, potassium hydroxide and lithium hydroxide; hydrides such as sodium hydride, potassium hydride, lithium hydride and calcium hydride; metals such as sodium; carbonates such as potassium carbonate, sodium carbonate, and lithium carbonate; alkoxides such as tert-butoxide, and isopropoxide; and bicarbonates such as lithium bicarbonate, sodium bicarbonate, and potassium bicarbonate; and mixtures thereof. More preferably the base is a hydroxide, still more preferably the base is selected from the group consisting of sodium hydroxide, potassium hydroxide, calcium hydroxide, magnesium hydroxide and lithium hydroxide, and most preferably the base is sodium hydroxide.

The preparation of mono-protected 1,2-diheteroethylene sulfonamide I can be carried out in the absence of substantially any solvent or it can be carried out in the presence of a reaction solvent. As used in this invention, "absence of substantially any solvent" means that the amount of solvent present is less than about 5% by volume (L) per kg of compound I (% vol/wt), preferably less than about 2% vol/wt, and more preferably less than about 1% vol/wt.

When the reaction solvent is present, it is preferred that the reaction solvent is a nonpolar solvent. As used in this invention a "nonpolar solvent" refers to a solvent having a dielectric constant of less than about 20, preferably less than about 15, more preferably less than about 10, and most preferably less than about 5. As used in this invention, the dielectric constant, $\epsilon$, of a solvent refers to the value at 20° C. The dielectric constant of a solvent can be found, for example, in Handbook of Chemistry and Physics, 63rd Ed., CRC Press, 1983, pp. E-51 to E-54, which is incorporated herein by reference. More preferable the reaction solvent is aprotic solvent, such as ethers and hydrocarbons. As used herein, an "aprotic solvent" refers to a solvent which is not a good hydrogen bond donor, i.e., solvents that do not contain heteroatom-hydrogen bond, e.g., O—H, or N—H bond. It should be appreciated, however, that while aprotic solvents are not good hydrogen bond donors, they may or may not be good hydrogen bond acceptors. Still more preferably the reaction solvent is selected from the group consisting of toluene, tetrahydrofuran and 2-methyltetrahydrofuran, and most preferably the reaction solvent is toluene.

The mono-protected 1,2-diheteroethylene sulfonamide I can be isolated from the reaction mixture by adding a sufficient amount of acid to the reaction mixture to neutralize any base that may be present, removing the reaction solvent and crystallizing or precipitating it from a crystallization solvent. Preferably, a sufficient amount of acid is added to the reaction mixture resulting in the pH of the solution from pH of about 5 to pH of about 7, more preferably, from pH of about 5 to pH of about 6, and most preferably from pH of about 5 to pH of about 5.5. Any acid having sufficient pKa to generate the desired pH can be used. Preferably the acid is selected from the group consisting of inorganic acids such as hydrochloric acid, hydriodic acid, hydrobromic acid, phosphoric acid and sulfuric acid, and more preferably the acid is hydrochloric acid. Preferably, the crystallization solvent is a lower alkyl alcohol, and more preferably ethanol. Preferably the crystallization solvent is maintained at a temperature of from about −25° C. to about 50° C. to crystallize the reaction product, more preferably from about −10° C. to about 25° C., and most preferably from about −5° C. and 10° C.

Unlike the process described in the Background section, one particular embodiment of the present invention provides a process for preparing a mono-protected ethylene glycol sulfonamide derivative of compound I (where X and Y are O) using a mono-protected ethylene glycol derivative which prevents formation of an undesired ethylene glycol bis-sulfonamide compound, e.g., where two molecules of compound II are coupled to one molecule of ethylene glycol to form a molecule of a general structure Ar—$OCH_2CH_2O$—Ar, wherein Ar is the portion of the compound II which has been coupled to ethylene glycol. Without being bound by any theory, it is believed that in the process described in the Background section, the hydroxy group of some of the initially formed ethylene glycol sulfonamide derivative reacts with unreacted sodium ethylene glycol ($NaOCH_2CH_2OH$) or other bases which may present in the reaction mixture to form an anion which then reacts with another molecule of pyrimidine mono-halide II to produce the undesired ethylene glycol bis-sulfonamide derivative. By using the mono-protected ethylene glycol derivative, the present invention eliminates any possibility of forming such an anion, thus completely eliminating production of the undesired ethylene glycol bis-sulfonamide derivative. This elimination of the production of undesired bis-sulfonamide ethylene glycol derivative results in higher overall product yield and easier product purification.

Another shortcoming in the process described in the Background section is the use of ethylene glycol as a solvent which must be removed by distillation after the reaction. In a small scale reaction, using ethylene glycol as a solvent does not pose much difficulty. In a large industrial scale reaction, however, using ethylene glycol is impracticable because of its toxicity and its high boiling point which requires a large amount of time and energy for its removal. In contrast, the process of the present invention uses a nonpolar solvent as discussed above.

The process for preparing the mono-protected 1,2-diheteroethylene sulfonamide I can further include a step of removing the protecting group, i.e., conversion of $R_5$ to hydrogen. Removal of a variety of protecting groups is disclosed in the above mentioned "Protecting Groups in Organic Synthesis."

As an illustration, the process for removing a protecting group of mono-protected ethylene glycol sulfonamide I will be discussed with regard to removing a tert-butyl ether protecting group of an alcohol (i.e., conversion of $R_5$ from tert-butyl to hydrogen, where X and Y are O). Contacting the tert-butyl ether protected ethylene glycol sulfonamide I (i.e., compound I wherein $YR_5$ is a O-tert-butyl moiety) with an acid removes the tert-butyl protecting group. Any acid having a sufficient acidic strength to remove tert-butyl ether group can be used. Exemplary acids include organic acids such as toluenesulfonic acid, trifluoroacetic acid (TFA), methanesulfonic acid (MSA), formic acid, acetic acid and other carboxylic acids; inorganic acids such as sulfuric acid, hydrobromic acid, hydriodic acid and hydrochloric acid; and Lewis acids such as $ZnCl_2$, $AlCl_3$, $FeCl_3$, $TiCl_4$, and $Me_3SiI$. Such acids can be used individually or as a mixture. Preferably the acid is selected from the group consisting of trifluoroacetic acid (TFA), methanesulfonic acid (MSA), formic acid, acetic acid, sulfuric acid, hydrochloric acid, $FeCl_3$, $TiCl_4$, and $Me_3SiI$, and more preferably the acid is formic acid.

When using a protic acid in the deprotection of an ether protecting group, it is preferred that an alcohol solvent is used in the deprotection reaction. As used in this invention, the term "protic acid" refers to a Bronsted-Lowry acid, i.e., any substance that is capable of giving up a hydrogen ion, or proton. Preferably, the alcohol solvent is selected from the group consisting of methanol, ethanol, iso-propanol and butanol, more preferably the alcohol solvent is selected from the group consisting of methanol, ethanol and iso-propanol, and most preferably the alcohol solvent is ethanol.

With regards to tert-butyl ether protected ethylene glycol sulfonamide I, a useful reaction temperature for the deprotection of an ether is from about 10° C. to about 125° C., more preferably from about 25° C. to about 100° C., and most preferably from about 80° C. to about 90° C. The ratio of the protic acid to the tert-butyl ether protected ethylene glycol sulfonamide I can be from about 1 liter of the acid:1 kilogram of the mono-protected compound (i.e., 1:1 (1/kg)) to about 10:1 (1/kg), preferably about 5:1 (1/kg), and most preferably about 2:1 (1/kg). Under these conditions, less than about 5% of residual tert-butyl ether protected ethylene glycol sulfonamide I remains after about 1 to 10 hours, and preferably less than about 1%. Preferably, the deprotection reaction results in less than about 1% of tert-butyl ether protected ethylene glycol sulfonamide I remaining.

After the deprotection reaction, the reaction mixture is cooled and a nonpolar aprotic solvent, as discussed above, is added. A substantial amount of nonpolar solvent and the protic acid is then removed, for example, by azeotropic distillation under a reduced pressure.

When formic acid is used for the deprotection of tert-butyl ether protected ethylene glycol sulfonamide I, the initial product can be a formyloxy-protected ethylene glycol sulfonamide I (i.e., compound I, wherein X and Y are O and $R_5$ is CHO). The formyloxy-protected ethylene glycol sulfonamide I is typically isolated from the reaction mixture by the following process. The reaction mixture containing formyloxy-protected ethylene glycol sulfonamide I is cooled to from about 25° C. to about 100° C., more preferably from about 35° C. to about 85° C., and most preferably to from about 45° C. to about 55° C. The resulting slurry is then diluted with an alcohol solvent, preferably ethanol, and heated to reflux. Cooling the resulting alcohol solvent mixture to from about −25° C. to about 25° C., preferably from about −15° C. to about 15° C., and more preferably from about −10° C. to about 0° C., affords the desired formyloxy-protected ethylene glycol sulfonamide I. In some cases, a solvated formyloxy-protected ethylene glycol sulfonamide I is obtained by this process, i.e., a solid formyloxy-protected ethylene glycol sulfonamide I containing solvent molecules, e.g., ethanol. The term "solvated" means a solid compound which contains solvent molecules within the crystal lattice of the compound.

Alternatively, the alcohol solvent mixture from above is cooled to from about 0° C. to about 50° C., more preferably from about 15° C. to about 35° C., and most preferably to about 25° C. The solvent is removed by decantation from a crystallized slurry containing product. Although the product may be dried, typically the wet product is used directly in the subsequent process.

The formyloxy group can then be removed by contacting the formyloxy-protected ethylene glycol sulfonamide with a base. Any base which can hydrolyze the formyloxy group can be used. Preferably the base is selected from the group consisting of hydroxides such as sodium hydroxide, potassium hydroxide, lithium hydroxide, calcium hydroxide and magnesium hydroxide; carbonates such as sodium carbonate, lithium carbonate, potassium carbonate and calcium carbonate; bicarbonates such as sodium bicarbonate, potassium bicarbonate and lithium bicarbonate. More preferably the base is selected from the group consisting of hydroxide, and most preferably sodium hydroxide. The deprotection of the formyloxy group can be performed in the presence of a solvent. Preferably, the solvent is a protic solvent such as water, alcohol and a mixture thereof, more preferably the solvent is water, ethanol and a mixture thereof.

For removal of the formyloxy group, typically the combined mixture is stirred at a temperature of from about 5° C. to about 65° C., more preferably from about 15° C. to about 45° C., and most preferably at about 25° C. The reaction time can range from about 5 minutes to about 48 hours, more preferably from about 15 minutes to about 5 hours, and most preferably from about 30 minutes to about 90 minutes. After the removal of formyloxy group, the reaction mixture is acidified to adjust the pH of the reaction mixture to pH of from about 5 to pH of about 7, more preferably to pH of from about 5 to pH of about 6, and most preferably to pH of from about 5 to pH of about 5.5. Any acid which is sufficiently strong enough to adjust the pH range of the reaction mixture to a desired pH can be used. Preferably the acid is hydrochloric acid, more preferably the acid is 12 N HCl solution. After the addition of acid, water is added and the suspension is stirred for from about 1 hour to about 10 hours, more preferably from about 2 hours to about 5 hours, and most preferably for about 3 hours. The solid product, ethylene glycol sulfonamide (i.e., compound I, wherein X and Y are O and $R_5$ is hydrogen), is then filtered, washed with an alcohol-water mixture, preferably ethanol-water mixture, and dried using standard process to afford the desired ethylene glycol sulfonamide.

The ethylene glycol sulfonamide can be further purified by refluxing the solution of the wet impure ethylene glycol sulfonamide in an alcohol, preferably ethanol, with the addition of water during the reflux. The resulting suspension is then cooled to a range from about 0° C. to about 50° C., more preferably from about 15° C. to about 35° C., most preferably from about 20° C. to about 30° C. The mixture is cooled to a desired temperature over a period of from about 1 hour to about 24 hours, more preferably from about 2 hours to about 12 hours, and most preferably from about 5 hours to about 7 hours. The purified ethylene glycol sulfonamide is then isolated and dried. Using this process, ethylene glycol sulfonamide having a purity of greater than about 99.3% can be produced, more preferably greater than about 99.5%, and most preferably greater than about 99.8%.

The process for preparing mono-protected 1,2-diheteroethylene sulfonamide I of the present invention can also include a process for preparing the pyrimidine monohalide II by contacting a pyrimidine dihalide III of the formula:

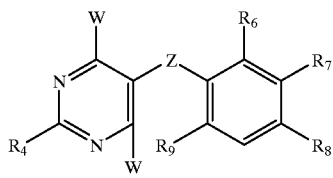

with a sulfonamide IV of the formula:

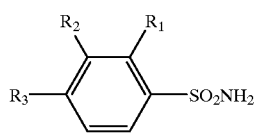

This coupling reaction between the pyrimidine dihalide III and the sulfonamide IV can include the presence of a base. Without being bound by any theory, it is believed that the base deprotonates the sulfonamide and neutralizes any acid that is generated during the reaction. It is believed that in the absence of a base, the resulting acid that is generated in the coupling reaction can reduce the rate of subsequent coupling reaction by protonating the sulfonamide IV thereby reducing its reactivity, or the acid can cause degradation of the product and/or starting material resulting in a decrease in the overall yield. It should be appreciated that in the presence of a base, the reactive species may be the deprotonated sulfonamide (i.e., sulfonamide anion). Thus, while the sulfonamide is represented in its neutral form, in the presence of a base, the process of the present invention also encompasses the corresponding sulfonamide anion. Preferably, the base is selected from the group consisting of sodium bicarbonate, potassium bicarbonate, lithium bicarbonate, sodium carbonate, potassium carbonate, lithium carbonate, sodium hydroxide, lithium hydroxide, calcium hydroxide, magnesium hydroxide and potassium hydroxide, more preferably the base is selected from the group consisting of potassium carbonate, sodium carbonate, sodium hydroxide and potassium hydroxide, and most preferably the base is potassium carbonate. The amount of base used in this reaction is from about 1 eq. to about 2 eq., preferably from about 1 eq. to about 1.5 eq., more preferably from about 1 eq. to about 1.3 eq., and most preferably about 1.1 eq.

This coupling reaction can be conducted in the same reaction solvent as the solvent used in the coupling reaction between the pyrimidine monohalide II and the mono-protected 1,2-diheteroethylene compound. Moreover, the reaction mixture of the coupling reaction between the pyrimidine dihalide III and the sulfonamide IV can be used directly in the next step without isolation or purification.

The coupling reaction between the pyrimidine dihalide III and the sulfonamide IV can also include the presence of a phase transfer catalyst. A "phase transfer catalyst" refers to a catalyst or agent which is added to a reaction mixture of components, to transfer one or more of the reacting components to a location where it can conveniently and rapidly react with another reacting component. Non-limiting examples of phase transfer catalysts or agents that may be employed are reviewed in "Phase-Transfer Catalysis," by C.M. Starks et al., Chapman & Hall, New York, N.Y., 1994, which is incorporated herein by reference in its entirety. Preferably the phase transfer catalyst is selected from the group consisting of tetrabutylammonium bromide, tetrabutylphosphonium bromide, tetrabutylammonium chloride, tetrabutylphosphonium chloride, benzyltriethylammonium chloride, and tetrabutylammonium hydrogen sulfate, and more preferably tetrabutylammonium bromide. Preferably from about 0.5 mole % to about 10 mole % of phase transfer catalyst is added to the reaction mixture, more preferably from about 1 mole % to about 5 mole %, still more preferably from about 1.5 mole % to about 2.5 mole %, and most preferably about 2 mole %.

Preferably the reaction time is from about 2 hours to about 15 hours, more preferably from about 5 hours to about 10 hours, and most preferably from about 5 hours to about 7 hours. The reaction can be conducted under a condition where any water that is present or formed in the reaction mixture is removed. For example, this can be achieved by using a reaction solvent which can remove water azeotropically using a Dean-Stark apparatus. Preferably the reaction solvent is same as the solvent used in the coupling reaction between the pyrimidine monohalide II and the mono-protected 1,2-diheteroethylene compound. Use of the same reaction solvent allows the coupling reaction between the pyrimidine monohalide II and the mono-protected 1,2-diheteroethylene compound to be conducted without isolating the product from the coupling reaction between the pyrimidine dihalide III and the sulfonamide IV. This elimination of a need for isolation of a product reduces the production time and overall cost. Moreover, it eliminates isolation of sensitizer pyrimidine monohalide II, thus reducing the risk of exposure to a harmful chemical.

The process for preparing mono-protected 1,2-diheteroethylene sulfonamide I of the present invention can also include a process for preparing a pyrimidine dihalide III by contacting pyrimidinedione V of the formula:

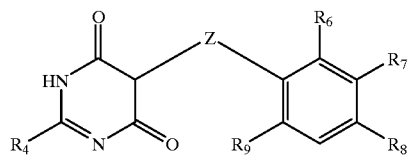

with a dehydrohalogenating reagent. As used in this invention, a "dehydrohalogenating reagent" refers to any reagent which is capable of converting the pyrimidinedione V to pyrimidine dihalide III. Exemplary dehydrohalogenating reagents include phosphorus oxychloride, phosphorous pentachloride, phosphorous trichloride, phosphorus oxybromide, phosphorous pentabromide, phosphorous tribromide, oxalyl chloride, and mixtures thereof. Preferably the dehydrohalogenating agent is selected from the group consisting of phosphorous oxychloride, phosphorous pentachloride, phosphorous trichloride, and mixtures thereof.

The conversion of pyrimidinedione V to pyrimidine dihalide III using a dehydrohalogenating agent is typically conducted at an elevated temperature. Preferably the reaction temperature is at least about 80° C., more preferably at least about 85° C., and most preferably at least about 90° C. Although the reaction can be conducted in any solvent which is substantially inert to the reaction conditions, typically the reaction is conducted in the absence of a solvent. After a sufficient amount of the pyrimidine dihalide III is formed, the reaction mixture is diluted with a solvent which has a boiling point of at least 80° C., preferably at least about 90° C., and more preferably at least about 110° C. Preferably the solvent is a nonpolar solvent, more preferably an aprotic nonpolar solvent, still more preferably toluene, and most preferably the same nonpolar solvent as that used in the subsequent process. By using the same nonpolar solvent as the subsequent process, the present invention avoids having to isolate and/or purify the pyrimidine dihalide III which is a known to be a potent sensitizer. The resulting reaction mixture is then quenched to destroy any remaining dehydrohalogenating agent. The quenching agent is any compound which reacts with the dehydrohalogenating agent without significantly reacting with pyrimidinedione V and/or pyrimidine dihalide III. Preferably the quenching agent is selected from an alcohol, water, and mixtures thereof. More preferably the quenching agent is water. The quenching agent can also contain a base to neutralize any acid that may be formed during the quenching step. Any base which can neutralize the acid that is formed in the quenching step can be used. Preferably the base is a hydroxide, and more preferably sodium hydroxide.

When a phosphorous compound is used as the dehydrohalogenating agent, phosphorous by-products are produced during the quenching step. The removal of these phosphorous by-products can be facilitated by adding a metal oxide. Preferably the metal oxide is selected from the group consisting of a transition metal oxide, alkali-earth metal oxide and alkali metal oxide, more preferably the metal oxide is selected from the group consisting of an alkaline-earth metal oxide, and most preferably the metal oxide is calcium oxide. The pyrimidine dihalide III can be isolated from the reaction mixture prior to the subsequent process; however, the pyrimidine dihalide III is believed to be a sensitizer. Therefore, it is preferred that the pyrimidine dihalide III be used in the subsequent process without first being isolated or purified.

Additional objects, advantages, and novel features of this invention will become apparent to those skilled in the art upon examination of the following examples thereof, which are not intended to be limiting.

EXAMPLES 4-tert-Butylbenzenesulfonamide (4) was purchased from Saurefabrik Schweizerhall. Phosphorus oxychloride, potassium carbonate, tetrabutylammonium bromide, sodium hydroxide beads, and formic acid were purchased from Aldrich Chemical Company. Toluene was purchased from Burdick and Jackson. Ethylene glycol mono tert-butyl ether (ETB) was purchased from TCI America. Ethanol was purchased from Spectrum Chemical.

Ethylene glycol mono-tert-butyl ether is also available from Maruzen, and Spectrum.

All other reagents and solvents are readily commercially available, for example from Aldrich Chemical Company or equivalent commercial suppliers.

EXAMPLE 1

This example illustrates the preparation of 4,6-dichloro-5-(O-methoxy-phenoxy)-2,2'-bipyrimidine (3).

A mixture of 150.0 g (0.480 mol) of 5-(O-methoxy-phenoxy)-2-(2-pyrimidin-2-yl)-4,6 (1H, 5H)-pyrimidine dione (2) and 176 mL (290 g, 1.89 mol) phosphorus oxychloride was heated to 90° C. After the vigorous gas evolution subsided, the pot temperature was increased to 105° C. and maintained there for 5 h. The mixture was cooled to 80–90° C., diluted with 225 mL toluene then added via a 12 gauge cannula to a mixture of 675 mL toluene and 525 mL $H_2O$ over 15–30 min. External cooling is used to maintain the quench mixture temperature at less than 80° C. Aqueous sodium hydroxide (400 mL of 30%) was added at 70–80° C. then the layers were separated. The toluene layer was washed with 500 mL of water containing 1 mL of 30% aq NaOH. To avoid precipitation of dichloropyrimidine (3) the temperature must be kept above 70° C. after the caustic addition.

The combined aqueous layers were extracted with 500 mL toluene. The combined organic phases were dried by distillation of the toluene azeotrope. The resulting solution was used directly in the next step.

EXAMPLE 2

This example illustrates the preparation of p-tert-butyl-N-[6-chloro-5-(O-methoxy-phenoxy) [2,2'-bipyrimidin]-4-yl] benzenesulfonamide potassium salt (5) using BTEAC.

A mixture of 6.427 g (30.13 mmol) of 4-tert-butylbenzenesulfonamide (4), anhydrous potassium carbonate (Armand, extra fine grade, 4.997 g, 36.16 mmol, 1.2 equiv.), 69 mg (0.301 mmol, 1 mole %) benzyltriethylammonium chloride (BTEAC), dichloropyrimidine (3) (10.521 g, 30.13 mmol) and toluene (150 mL) was refluxed (heating bath at 130° C., Dean-Stark trap) for 8 hours. The resulting mixture was cooled overnight.

To the stirred mixture was added 3.5 mL 12 N HCl (42 mmol) and water was removed by azeotropic distillation. Reaction analysis by HPLC showed 96.4% of the desired product after the acid work-up.

EXAMPLE 3

This example illustrates the preparation of p-tert-butyl-N-[6-chloro-5-(O-methoxy-phenoxy) [2,2'-bipyrimidin]-4-yl] benzenesulfonamide potassium salt (5) using TBAB.

4-tert-Butylbenzenesulfonamide (4) (102.4 g, 0.480 mol), 79.6 g (0.576 mol) anhydrous powdered (extra fine) potassium carbonate, 4.6 g (14 mmol, 2.9 mol %) tetrabutylammonium bromide (TBAB), and 1950 mL toluene were added to the toluene solution of dichloropyrimidine (3) at 50° C. The resulting suspension was refluxed with continuous removal of water using a Dean-Stark trap for 5–7 h. The suspension was cooled then used directly in the next step.

EXAMPLE 4

This example illustrates the preparation of p-tert-butyl-N-[6-(2-tert-butyl-ethoxy)-5-(O-methoxy-phenoxy) [2,2'-bipyrimidin]-4-yl] benzenesulfonamide (6).

Ethylene glycol mono-tert-butyl ether (ETB) (189 mL, 170 g, 1.44 mol) and 38.4 g (0.960 mol) of granular sodium hydroxide were added to the benzenesulfonamide potassium salt (5) suspension in toluene. The suspension was then heated at 55° C. for 3 to 7 h. The mixture changed from a slurry to a near solution to a suspension as the product precipitated near the end of the reaction. The suspension was cooled and 80 mL of 12 N HCl in 720 mL water was added. More acid (10–15 mL) was added to adjust the pH to 3–4 and produce two clear layers. The layers were separated. The organic layer was washed twice with 500 mL water.

The toluene-water azeotrope and toluene were distilled at atmospheric pressure (3,200 mL collected). The flask was cooled and distillation was continued under reduced pressure until approximately 50 mL of toluene remained. The pot solution was cooled and diluted with 1500 mL denatured ethanol. Toluene was removed as the ethanol azeotrope (500–750 mL collected) and the suspension allowed to cool to 25° C. overnight. After cooling to 2–5° C., the suspension was stirred for 2 h. The precipitate was suction filtered, washed with 500 mL cold denatured ethanol, then dried in a vacuum oven at 40–50° C. to afford 268 g (91.8%) of near colorless powder.

Recrystallization from toluene then ethyl ether provided material for elemental analysis: mp 156–156.5° C.; 300 MHZ $^1$H NMR (CDCl$_3$) δ 1.13 (s, 9H), 1.28 (s, 9H), 3.62 (t, 2H, J=4.9 Hz), 3.99 (s, 3H), 4.62 (t, 2H, J=4.9 Hz), 6.83–6.88 (m, 1H), 6.96–6.99 (d, 1H, J=8.1 Hz), 7.08–7.13 (m, 1H), 7.29 (d, 1H, J=8.1 Hz), 7.38–7.42 (m, 3H), 8.38 (d, 2H, J=8.6 Hz), 8.98 (d, 2H), 9.1 (br, 1H); IR (KBr pellet) 3300–3200, 2975, 2890, 2840, 1575, 1500 cm$^{-1}$. Anal Calcd for $C_{31}H_{37}N_5O_6S$: C, 61.27; H, 6.14; N, 11.52. Found: C, 61.53; H, 6.37; N, 11.42.

EXAMPLE 5

This example illustrates the preparation of p-tert-butyl-N-[6-(2-formyloxy-ethoxy)-5-(O-methoxy-phenoxy) [2,2'-bipyrimidin]-4-yl] benzenesulfonamide monoethyl alcohol solvate (8).

A mixture of p-tert-butyl-N-[6-(2-tert-butyl-ethoxy)-5-(O-methoxy-phenoxy) [2,2'-bipyrimidin]-4-yl] benzenesulfonamide (6) (250.82 g, 0.413 mol) and 500 mL 95–97% formic acid was heated at 85° C. for 4 h. The resulting yellow solution was cooled and diluted with 800 mL toluene. Formic acid and toluene were distilled as the azeotrope using a 1000 mL distillation storage head [Ace Glass catalog # 6620-14] as a layer-separating collector at 35–39° C. and 97–102 mm Hg (collected 680 mL top phase and 450 mL bottom phase).

At this point gas chromatography (GC) analysis indicates the toluene distillate contains only trace formic acid and the product-toluene ratio (LC area %) was ~92:4. The suspension was cooled to 50° C., diluted with 615 mL of absolute ethanol, then heated to reflux. The solution was allowed to cool to 25° C. at ~150 rpm over 18 h. The resulting suspension was cooled to −5° C., stirred for 2 h, then decanted (collected 400 mL in 75 min). The wet solid was taken up in 500 mL of absolute ethanol at reflux. The solution was allowed to cool to 25° C. at ~150 rpm over 4 h then the suspension was decanted (585 mL in 40 min). The wet solid was used directly in the next step.

Recrystallization from anhydrous ethanol provided material for elemental analysis: mp 138.5–140° C.; 300 MHZ $^1$H NMR (CDCl$_3$) δ 1.21 (t, 3H, J=7.0 Hz), 1.29 (s, 9H), 1.67 (br, 1H), 3.70 (m, 2H), 3.90 (s, 3H), 4.35 (m, 2H), 4.71 (m, 2H), 6.80–6.85 (m, 1H), 6.95 (d, 1H, J=7.5 Hz), 7.03–7.11 (m, 2H), 7.40–7.44 (m, 3H), 7.89 (s, 1H), 8.41 (d, 2H, J=8.4 Hz), 8.93 (br, 1H), 8.99 (d, 2H); IR (KBr pellet) 3600–3240, 2970, 2910, 2870, 1725, 1685, 1580, 1560 cm$^{-1}$. Anal Calcd for $C_{30}H_{35}N_5O_8S$: C, 57.59; H, 5.64; N, 11.19. Found: C, 57.40; H, 5.51; N, 11.43.

EXAMPLE 6

This example illustrates the preparation of p-tert-butyl-N-[6-(2-formyloxy-ethoxy)-5-(O-methoxy-phenoxy) [2,2'-bipyrimidin]-4-yl] benzenesulfonamide (7).

A mixture of p-tert-butyl-N-[6-(2-tert-butyl-ethoxy)-5-(O-methoxy-phenoxy) [2,2'-bipyrimidin]-4-yl] benzenesulfonamide (6) (47.692 g, 71.84 mmol) and 78 mL of 96% formic acid was heated at 90° C. for 3 hours. The resulting yellow solution, containing some black specs, was cooled to 25° C. and the volatiles were removed on a roto-evaporator at 45° C., and then on a vacuum pump overnight. The residual syrup was taken up in 200 mL ethyl acetate. The suspension was suction filtered, and the precipitate was washed with 50 mL ethyl acetate.

The mother liquors were concentrated on a rotary evaporator at 35° C. and the residue was triturated with 200 mL ethyl ether. The precipitate was suction filtered, then washed with 50 mL ethyl ether. The potassium formate was dried in vacuo for 20 hours at 25° C. to afford 5.11 g of colorless solid. The Bosentan formate (7) was dried in vacuo for 20 hours at 25° C. to afford 45.028 g of colorless solid. Theoretical yield of the potassium formate: 6.044 g. Theoretical yield of Bosentan formate (7): 41.644 g.

EXAMPLE 7

This example illustrates the preparation of Bosentan (1).

Absolute ethanol (600 mL), 165.2 g of 30% sodium hydroxide (1.239 mol NaOH), and 175 mL water were added to the wet p-tert-butyl-N-[6-(2-formyloxy-ethoxy)-5-(O-methoxy-phenoxy) [2,2'-bipyrimidin]-4-yl] benzenesulfonamide monoethyl alcohol solvate (8). The resulting solution was stirred at 25° C. for 60 min. The suspension was slowly acidified with 77 mL of 12 N HCl to pH 5 with ice cooling to maintain 25° C. Water (350 mL) was added dropwise then the suspension was stirred at 25° C. for 3 h. The precipitate was suction filtered, washed with 250 mL of 1:1 ethanol-water then briefly air dried at 25° C.

EXAMPLE 8

This example illustrates the purification of Bosentan (1).

The wet crude Bosentan (1) from Example 7 was taken up in 650 mL anhydrous ethanol at reflux. Water (650 mL) was added dropwise at reflux. The resulting suspension was allowed to cool to 25° C. at ~150 rpm over 6 h. The precipitate was suction filtered and air dried at 25° C. for 16 h to afford 214.47 g of near colorless crystals (91.2% from p-tert-butyl-N-[6-(2-tert-butyl-ethoxy)-5-(O-methoxy-phenoxy) [2,2'-bipyrimidin]-4-yl] benzenesulfonamide (6)).

EXAMPLE 9

This example illustrates the preparation of p-tert-butyl-N-[6-chloro-5-(O-methoxy-phenoxy) [2,2'-bipyrimidin]-4-yl] benzenesulfonamide sodium salt.

Into a 100 mL 3-neck Morton flask with condenser, nitrogen adapter, and overhead mechanical stirrer was added 4-tert-butylbenzenesulfonamide (1.851 g, 8.68 mmol), 4,6-dichloro-5-(O-methoxy-phenoxy)-2,2'-bipyrimidine (3) (3.121 g, 8.93 mmol), and anhydrous sodium carbonate (2.305 g, 21.75 mmol). The flask was sealed and the atmosphere was changed to dry nitrogen through 10 nitrogen-vacuum purge cycles.

2-Methyltetrahydrofuran (30 mL) was added via syringe and the suspension was refluxed for 25 hours at an external bath temperature of 80° C. At approximately 23.5 hours, at reflux, 190 mg of tetrabutyl ammonium bromide (TBAB) was added followed by another 810 mg TBAB. Reaction progress was followed by TLC (EtOAc) for a total of 24 hours. The suspension appears identical to that formed by the corresponding potassium salt.

EXAMPLE 10

This example illustrates the precipitation of phosphate from the aqueous waste of a reaction for preparing 4,6-dichloro-5-(O-methoxy-phenoxy)-2,2'-bipyrimidine (3).

The aqueous layers from the pyrimidinedichloride (3) workup (50 g scale) were combined then filtered though 0.45 micron media to yield 650 mL of a clear, light yellow solution containing about 0.985 M phosphate (as $PO_4^{-2}$).

The filtrate (100 mL) was charged to a 500 mL flask equipped with an overhead stirrer. After calcium oxide (3, 4, or 5 equivalents) was added, the white slurry was agitated vigorously for 30 to 60 minutes at 20–22° C. and then filtered through a coarse sintered glass funnel.

The slurries produced using 3 or 4 equivalents of calcium oxide both filtered well. Soluble phosphate was reduced from over 40,000 ppm to 4 ppm using 3 equivalents of calcium oxide. Soluble phosphate was reduced to just 1 ppm using 4 equivalents of calcium oxide.

Those skilled in the art will appreciate that numerous changes and modifications may be made to the preferred embodiments of the invention and that such changes and modifications may be made without departing from the spirit and scope of the invention. It is therefore intended that the appended claims cover all such equivalent variations as fall within the true spirit and scope of the invention.

What is claimed is:

1. A process for preparing a 1,2-diheteroethylene sulfonamide of the formula:

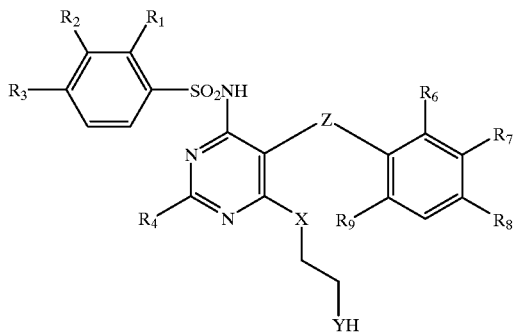

comprising:

(a) contacting a pyrimidine monohalide of the formula:

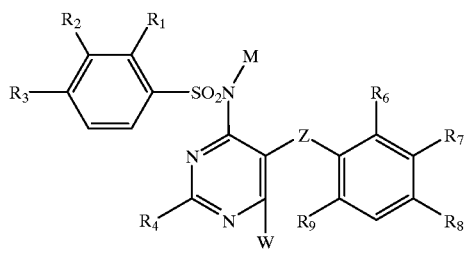

with a mono-protected 1,2-diheteroethylene anion of the formula $M_1XCH_2CH_2YR_5$ in an aprotic nonpolar solvent to produce a mono-protected 1,2-diheteroethylene sulfonamide of the formula:

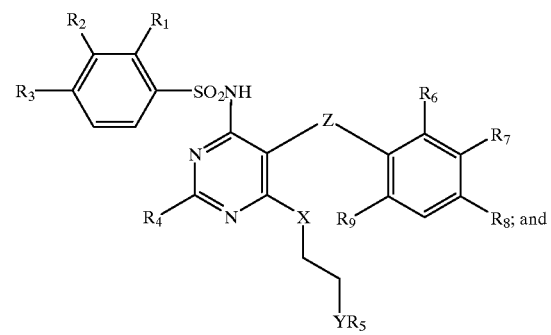

(b) removing $R_5$ group to produce said 1,2-diheteroethylene sulfonamide, wherein $R_1$ is hydrogen, lower alkyl, lower alkoxy, lower alkylthio, halogen or trifluoromethyl;

$R_2$ is hydrogen, halogen, lower alkoxy, trifluoromethyl or $OCH_2COOR_a$; and $R_3$ is hydrogen, halogen, lower alkyl, lower alkylthio, trifluoromethyl, cycloalkyl, lower alkoxy or trifluoromethoxy; or $R_2$ and $R_3$ together can be butadienyl, methylenedioxy, ethylenedioxy or isopropylidenedioxy;

$R_4$ is hydrogen, lower alkyl, cycloalkyl, trifluoromethyl, lower alkoxy, lower alkylthio, lower alkylthio-lower alkyl, hydroxy-lower alkyl, hydroxy-lower alkoxy, lower alkoxy-lower alkyl, hydroxy-lower alkoxy-lower alkyl, hydroxy-lower alkoxy-lower alkoxy, lower alkylsulfinyl, lower alkylsulfonyl, 2-methoxy-3-hydroxypropoxy, 2-hydroxy-3-phenylpropyl, amino-lower alkyl, lower alkylamino-lower alkyl, di-lower alkylamino-lower alkyl, amino, lower alkyl-amino, di-lower alkylamino, arylamino, aryl, arylthio, aryloxy, aryl-lower alkyl or heterocyclyl;

$R_5$ is a protecting group;

$R_6$, $R_7$, $R_8$ and $R_9$ are independently hydrogen, halogen, lower alkyl, trifluoromethyl, lower alkoxy, lower alkylthio, hydroxy, hydroxymethyl, cyano, carboxyl, formyl, methylsulfinyl, methylsulfonyl, methylsulfonyloxy or lower alkyloxy-carbonyloxy; or $R_7$ together with $R_6$ or $R_8$ can be butadienyl, methylenedioxy, ethylenedioxy or isopropylidenedioxy;

Z is O, S, ethylene, vinylene, C(=O), OCHR$_{10}$, or SCHR$_{10}$;

$R_{10}$ is hydrogen or lower alkyl;

X and Y are independently O, S or NH;

M is hydrogen, an alkaline metal or an alkaline earth metal;

$M_1$ is an alkaline metal or an alkaline earth metal; and

W is halide.

2. The process of claim 1, wherein said aprotic nonpolar reaction solvent is toluene.

3. The process of claim 1, further comprising the step of producing said pyrimidine monohalide, wherein said step comprises contacting a pyrimidine dihalide of the formula:

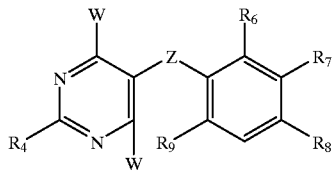

with a sulfonamide of the formula:

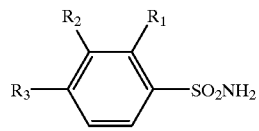

in a nonpolar solvent in the presence of a base and a phase transfer catalyst to produce said pyrimidine monohalide.

4. The process of claim 3, wherein said base is potassium carbonate.

5. The process of claim 3, wherein said phase transfer catalyst is selected from the group consisting of tetrabutylammonium bromide, tetrabutylphosphonium bromide, tetrabutylammonium chloride, tetrabutylphosphonium chloride, benzyltriethylammonium chloride, and tetrabutylammonium hydrogen sulfate.

6. The process of claim 3, wherein said nonpolar solvent is toluene.

7. The process of claim 3, wherein said pyrimidine monohalide is used in the subsequent step without isolation.

8. The process of claim 3, further comprising the step of producing said pyrimidine dihalide, wherein said step comprises contacting a pyrimidinedione of the formula:

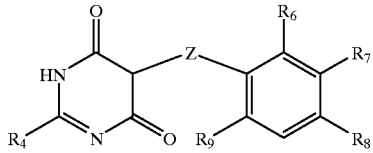

with a dehydrohalogenating agent to produce said pyrimldine dihalide.

9. The process of claim 8, wherein said pyrimidine dihalide is used in the subsequent step without isolation.

10. The process of claim 8, wherein said halide is chloride.

11. The process of claim 10, wherein said dehydrohalogenating agent selected from the group consisting of phosphorous oxychloride, phosphorous pentachloride, phosphorous trichloride, oxalyl chloride and mixtures thereof.

12. The process of claim 1, wherein X and Y are O.

13. The process of claim 12, wherein $R_5$ is tert-butyl.

14. The process of claim 13, wherein said step of removing $R_5$ group comprises contacting said mono-protected 1,2-diheteroethylene sulfonamide with an acid.

15. The process of claim 14, wherein said acid is formic acid.

16. The process of claim 15, wherein said step of contacting said mono-protected 1,2-diheteroethylene sulfonamide with said formic acid produces an intermediate mono-protected 1,2-diheteroethylene sulfonamide of the formula:

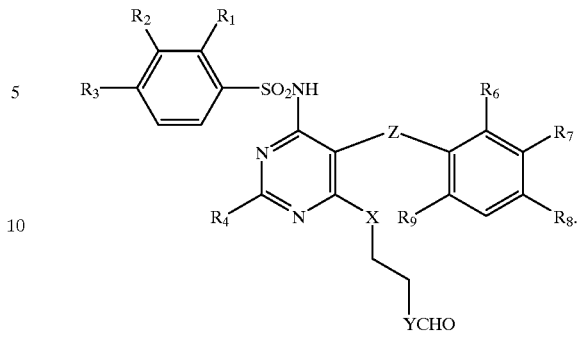

17. The process of claim 16, further comprising contacting said intermediate mono-protected 1,2-diheteroethylene sulfonamide with a base to produce said 1,2-diheteroethylene sulfonamide.

18. A process for preparing an ethylene glycol sulfonamide of the formula:

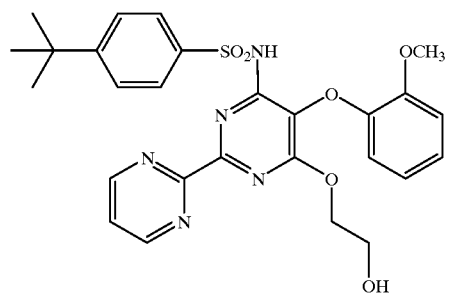

comprising:

(a) contacting a pyrimidinedione of the formula:

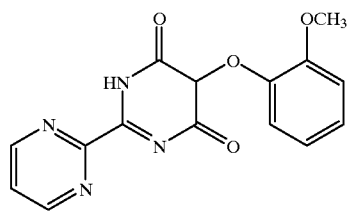

with a dehydrohalogenating agent to produce a pyrimidine dihalide of the formula:

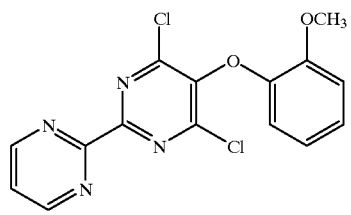

(b) contacting said pyrimidine dihalide with a sulfonamide of the formula:

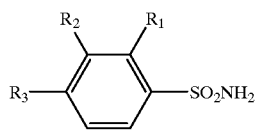

in a nonpolar aprotic solvent in the presence of a first base and a phase transfer catalyst to produce a pyrimidine monohalide of the formula:

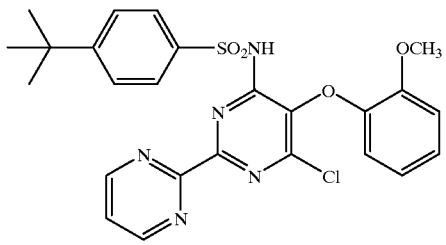

(c) contacting said pyrimidine monohalide with a mono-protected ethylene glycol of the formula $HOCH_2CH_2OR_5$ in said nonpolar aprotic solvent in the presence of a second base to produce a mono-protected ethylene glycol sulfonamide of the formula:

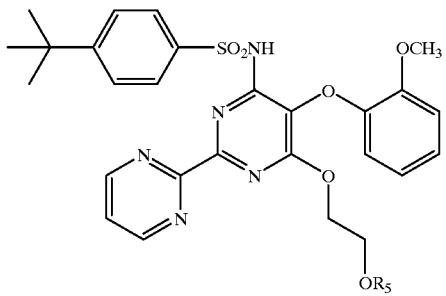

wherein
$R_5$ is a hydroxy protecting group; and
(d) removing the hydroxy protecting group to produce said ethylene glycol sulfonamide.

19. The process of claim 18, wherein said dehydrohalogenating agent selected from the group consisting of phosphorous oxychloride, phosphorous pentachloride, phosphorous trichloride, oxalyl chloride and mixtures thereof.

20. The process of claim 18, wherein said first base is potassium carbonate.

21. The process of claim 18, wherein said first base is present in the amount of from about 1 equiv. to about 2 equiv.

22. The process of claim 18, wherein said phase transfer catalyst is selected from the group consisting of tetrabutylammonium bromide, tetrabutylphosphonium bromide, tetrabutylammonium chloride, tetrabutylphosphonium chloride, benzyltriethylammonium chloride, and tetrabutylammonium hydrogen sulfate.

23. The process of claim 18, wherein said phase transfer catalyst is present in the amount of from about 0.5 mole % to about 10 mole % of said pyrimidine dihalide.

24. The process of claim 18, wherein said second base is sodium hydroxide.

25. The process of claim 18, wherein said nonpolar aprotic solvent is toluene.

26. The process of claim 18, wherein said $R_5$ is tert-butyl.

27. The process of claim 26, wherein said step of removing the protecting group comprises:
(e) contacting said mono-protected ethylene glycol sulfonamide with formic acid; and
(f) contacting the resulting product of said step (e) with a third base to produce said ethylene glycol sulfonamide.

28. The process of claim 27, wherein said third base is sodium hydroxide.

29. The process of claim 18, wherein said steps (a)–(c) are conducted without any isolation of each resulting compounds.

30. A compound selected from the group consisting of p-tert-butyl-N-[6-(2-tert-butoxyethoxy)-5-(o-methoxyphenoxy)-2-(pyrimidin-2-yl)-pyrimidin-4-yl] benzenesulfonamide, p-tert-butyl-N-[6-(2-formyloxyethoxy)-5-(o-methoxyphenoxy)-2-(pyrimidin-2-yl)-pyrimidin-4-yl] benzenesulfonamide, p-tert-butyl--N-[6-(2-formyloxyethoxy)-5-(o-methoxyphenoxy)-2-(pyrimidin-2-yl)-pyrimidin-4-yl] benzenesulfonamide monoethyl alcohol solvate in a crystalline form, and p-tert-butyl-N-[6-chloro-5-(o-methoxyphenoxy)-2-(pyrimidin-2-yl)-pyrimidin-4-yl] benzenesulfonamide potassium salt.

* * * * *